US010469043B2

United States Patent
Ko et al.

(10) Patent No.: US 10,469,043 B2
(45) Date of Patent: Nov. 5, 2019

(54) CLASS AB COMMON-SOURCE AMPLIFIER WITH CONSTANT TRANSCONDUCTANCE

(71) Applicant: Microchip Technology Incorporated, Chandler, AZ (US)

(72) Inventors: Isaac Ko, Kwun Tong (HK); Ka Wai Ho, Diamond Hill (HK); Wan Tim Chan, Yuen Long (HK)

(73) Assignee: Microchip Technology Incorporated, Chandler, AZ (US)

( * ) Notice: Subject to any disclaimer, the term of this patent is extended or adjusted under 35 U.S.C. 154(b) by 350 days.

(21) Appl. No.: 15/461,667

(22) Filed: Mar. 17, 2017

(65) Prior Publication Data

US 2017/0279423 A1    Sep. 28, 2017

Related U.S. Application Data

(60) Provisional application No. 62/311,468, filed on Mar. 22, 2016.

(51) Int. Cl.
| | |
|---|---|
| *H03F 3/26* | (2006.01) |
| *A61B 8/00* | (2006.01) |
| *H03B 5/32* | (2006.01) |
| *H03F 1/32* | (2006.01) |
| *H03F 3/30* | (2006.01) |

(52) U.S. Cl.
CPC ............ *H03F 3/265* (2013.01); *A61B 8/4272* (2013.01); *A61B 8/4483* (2013.01); *H03B 5/32* (2013.01); *H03F 1/3205* (2013.01); *H03F 3/3023* (2013.01); *H03F 2200/261* (2013.01); *H03F 2200/372* (2013.01); *H03F 2200/498* (2013.01); *H03F 2200/75* (2013.01)

(58) Field of Classification Search
CPC ..................................................... H03F 3/265
See application file for complete search history.

(56) References Cited

U.S. PATENT DOCUMENTS

| | | | | |
|---|---|---|---|---|
| 3,484,867 A | * | 12/1969 | Babcock | ................ H03F 1/307 330/266 |
| 4,118,731 A | * | 10/1978 | Hinn | ..................... H04N 9/648 348/809 |
| 5,151,085 A | * | 9/1992 | Sakurai | ................. A61B 8/546 310/316.02 |
| 7,076,070 B2 | * | 7/2006 | Pearce | ............... H01L 21/8234 257/368 |
| 2010/0171552 A1 | * | 7/2010 | French | ................. H03F 1/0227 330/123 |

FOREIGN PATENT DOCUMENTS

| | | |
|---|---|---|
| JP | 2008188321 A | 8/2008 |
| JP | 2009297128 A | 12/2009 |

OTHER PUBLICATIONS

European Patent Office, International Search Report for International Application No. PCT/US2017/023328, dated Jun. 6, 2017.

* cited by examiner

*Primary Examiner* — Patricia T Nguyen
(74) *Attorney, Agent, or Firm* — Burr & Forman LLP; Ryan M. Corbett

(57) ABSTRACT

An ultrasound probe buffer is provided. The ultrasound probe buffer may include a high impedance amplifier having a common-source core stage with series-series local feedback. The high impedance amplifier may include a first MOSFET and a second MOSFET, wherein a source terminal of the first MOSFET is coupled to a source terminal of the second MOSFET.

6 Claims, 7 Drawing Sheets

Proposed Push-Pull Class AB CS Amplifier with Constant Transconductance

**Single Channel Block Diagram

Proposed Push-Pull Class AB CS Amplifier with Constant Transconductance

Frequency Response of the Proposed Class AB Probe Buffer with Flat Transconductance from 1MHz to 100MHz Current Output with 5MHz ±500mV Input Signal, HD2 = -60.2dBc Input referred voltage noise power spectral density, VN = 1.38nV/√Hz @5MHz Input referred current noise power spectral density, IN = 0.28pA/√Hz @5MHz

US 10,469,043 B2

CLASS AB COMMON-SOURCE AMPLIFIER WITH CONSTANT TRANSCONDUCTANCE

CROSS-REFERENCE TO RELATED APPLICATION

This application claims the benefit of U.S. Provisional Patent Application No. 62/311,468, filed on Mar. 22, 2016, which is incorporated herein by reference in its entirety.

TECHNICAL FIELD

The present disclosure generally relates to a low distortion, low noise and low power ultrasound probe buffer.

SUMMARY

Ultrasonic transducers are commonly used in a variety of fields, including the medical field. For example, ultrasonic transducers can be used to make cross-sectional images of various parts of the body for diagnostic purposes. At a high level, ultrasonic transducers operate by converting electrical signals into ultrasonic waves which are transmitted toward an object to be analyzed. The ultrasonic waves are reflected by the object, the transducer detects the reflected waves, and converts the detected waves into electrical signals that may be analyzed to determine characteristics of the object of interest.

In practice, arrays of transducers are often arranged in a handle that a medical professional uses to direct the ultrasonic waves toward a patient. The handle is coupled to a wire, such as a coaxial cable, which is in turn coupled to the system that causes the transducers in the handle to transmit the ultrasonic waves and analyzes the signals received by the transducer. FIG. 1 shows a block diagram of an exemplary ultrasonic transducer having a transducer handle coupled to a cable, which is coupled to the transducer system. However, the transducer handle may transmit insufficient electrical signal power to drive the cable. Therefore, a mechanism that boosts the electrical signal power from the transducer to drive the cable is needed.

A transducer element may be made from PZT material which can be electrically modeled using a crystal resonator model, as shown in FIG. 1a. The values of the circuit elements may vary depending on the size and shape of the transducer elements, however, the elements of the circuit shown in FIG. 1a may have values in the following ranges: C=10 pF to 250 pF; L=5 µH to 35 µH; R=100Ω to 500Ω; and $C_n$=15 pF to 450 pF.

While a transimpedance amplifier may have a low input impedance, which is desirable to maximize the received current signal, it is not suitable for electrical impedance matching. Electrical impedance matching at the receiver may be needed to reduce reflections of the incoming acoustic energy back to the medium.

A common-source single or two-stage voltage, transconductance or charge amplifier would be suitable for voltage sensing, but when used as a probe buffer would limit the bandwidth. As the PZT transducer is narrow-band in nature, in order to match the electrical impedance of the probe buffer to that of the transducer, according to an aspect of one or more exemplary embodiments, there is provided a high input impedance transconductance amplifier that may be implemented with a common-source core stage with series-series local feedback for low distortion and low-noise performance. Because the transducer may have a high output impedance, the analog front end probe buffer is preferably a high-precision amplifier with very low input referred current and voltage noise to acquire a very low magnitude output from the transducer.

According to an aspect of one or more exemplary embodiments, there is provided an ultrasound probe buffer that may include a common-source class AB low-noise transconductance amplifier having large input impedance and constant transconductance. One or more exemplary embodiments may also relate to a low power receive transconductor probe buffer for use in medical ultrasound transducer handles. The exemplary embodiments may be used to improve system performance, primarily receive noise and bandwidth, by driving the transducer cable back to the system.

The ultrasound probe buffer according to one or more exemplary embodiments may include a high impedance amplifier having a common-source core stage with series-series local feedback. The high impedance amplifier may include a first MOSFET and a second MOSFET, wherein a source terminal of the first MOSFET is coupled to a source terminal of the second MOSFET.

The high impedance amplifier may also include a first source degeneration resistor coupled to a drain terminal of the first MOSFET, and a second source degeneration resistor coupled to a drain terminal of the second MOSFET. The resistance of the first source degeneration resistor may be equal to the resistance of the second source degeneration resistor.

The ultrasound probe buffer may also include an operational amplifier having a first input coupled to the source terminal of the first MOSFET and the source terminal of the second MOSFET. An output of the operational amplifier may be coupled between the drain terminal of the second MOSFET and the second source degeneration resistor. The output of the operational amplifier may be coupled to a gate terminal of the second MOSFET.

The high impedance amplifier may output an output current from the source terminals of the first MOSFET and the second MOSFET. The gate terminal of the first MOSFET may be coupled to a gate terminal of the second MOSFET via at least one capacitor. The first MOSFET may be a p-type MOSFET and the second MOSFET may be an n-type MOSFET. The transconductance of the ultrasound probe buffer may be substantially constant.

DETAILED DESCRIPTION OF EXEMPLARY EMBODIMENTS

Figure 1:
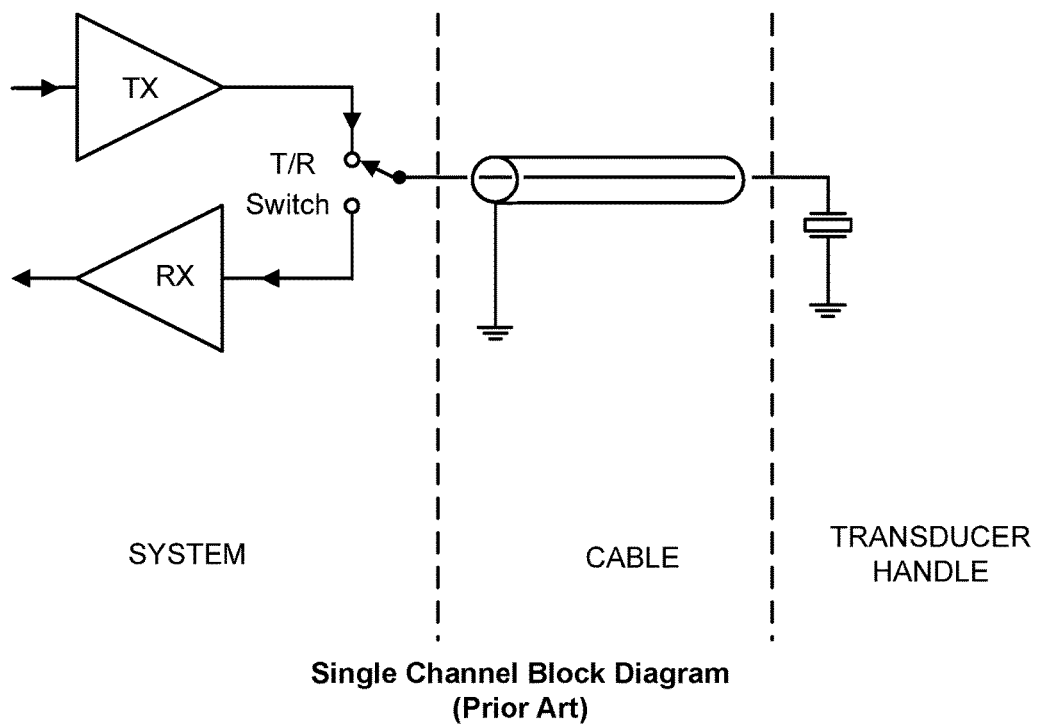
FIG. 1 depicts a block diagram of a single channel ultrasonic transducer according to the related art.
Figure 1A:
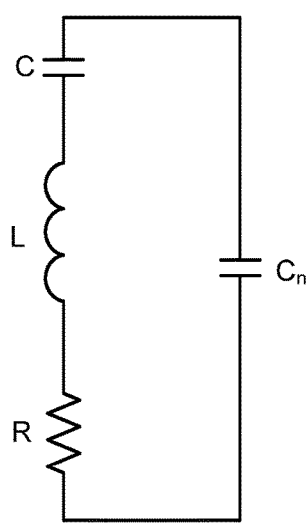
FIG. 1a depicts a crystal resonator model of a transducer element according to one or more exemplary embodiments.

Reference will now be made in detail to the following exemplary embodiments, which are illustrated in the accompanying drawings, wherein like reference numerals refer to like elements throughout. The exemplary embodiments may be embodied in various forms without being limited to the exemplary embodiments set forth herein. Descriptions of well-known parts are omitted for clarity.

Figure 2:
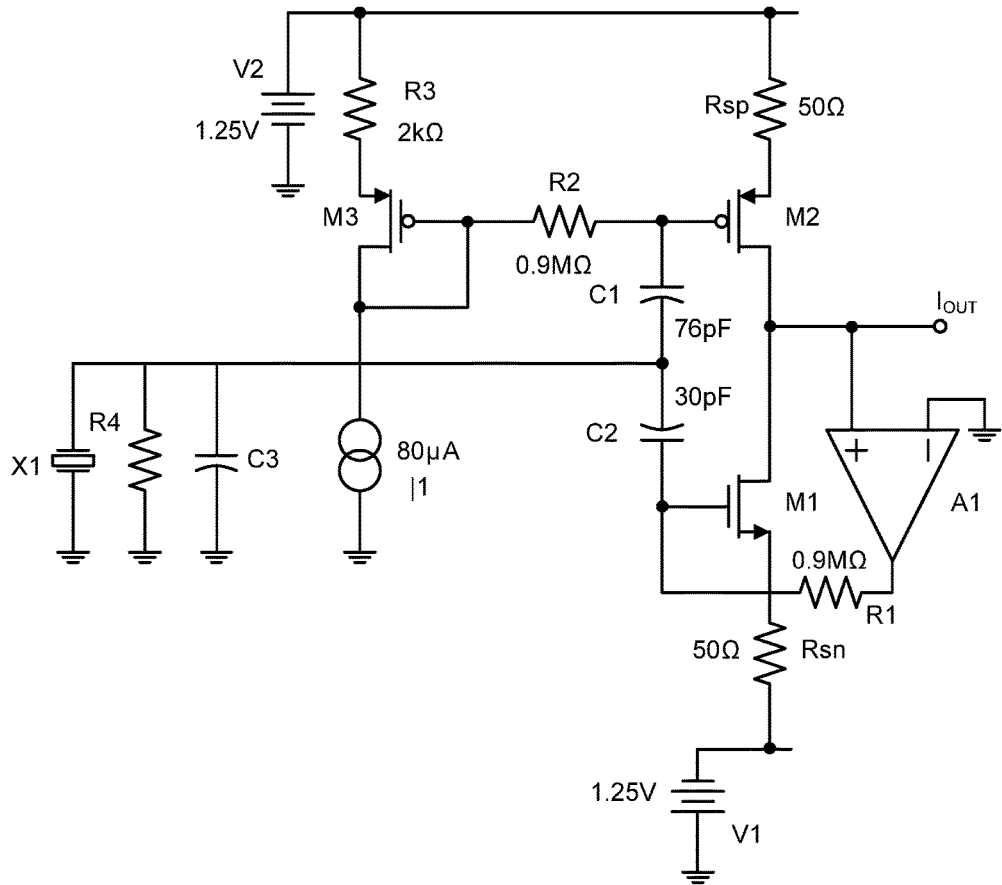
FIG. 2 depicts a push-pull class AB common-source amplifier according to one or more exemplary embodiments.
Figure 3:
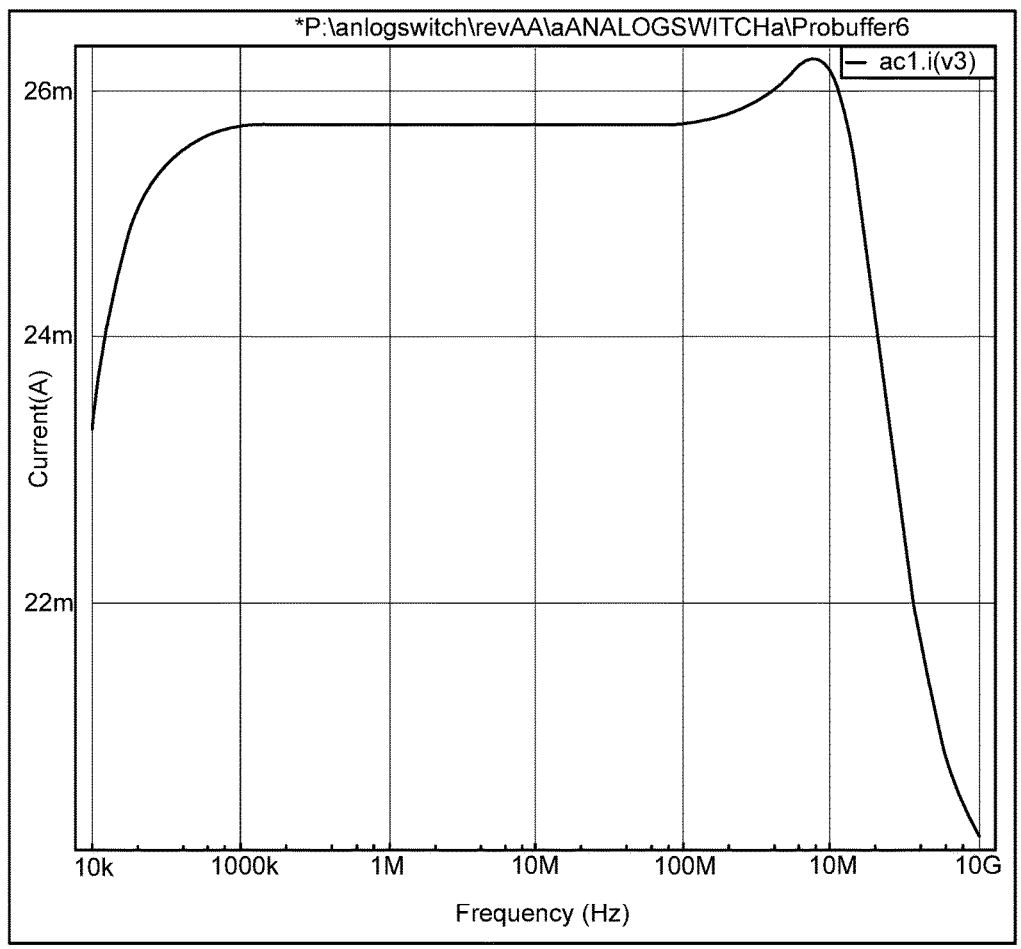
FIG. 3 depicts the frequency response of the amplifier depicted in FIG. 2.
Figure 4:
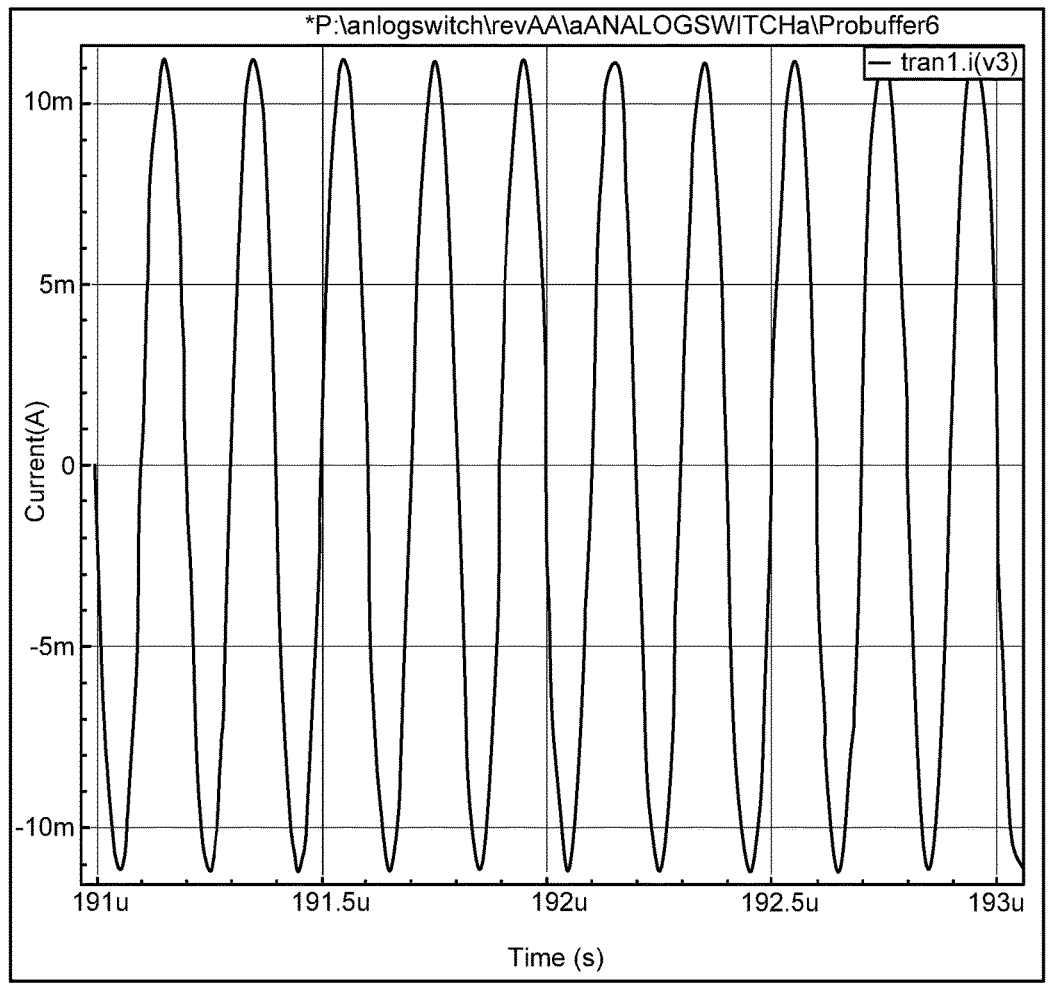
FIG. 4 depicts the output current of the amplifier depicted in FIG. 2.

FIG. 2 depicts a push-pull class AB common-source amplifier according to one or more exemplary embodiments. As shown in FIGS. 2-4, two complimentary common-source MOSFETs M1 and M2 with their source degeneration resistors may achieve wide bandwidth and high linearity. Referring to FIG. 2, the amplifier according to the exemplary embodiment may include MOSFETs M1 and M2. MOSFET M1 may be an n-type MOSFET and MOSFET M2 may be a p-type MOSFET. The drain terminals of M1 and M2 may be coupled together where the output current $I_{OUT}$ is output. The source terminal of M2 may be coupled to resistor $R_{SP}$, and the source terminal of M1 may be coupled to resistor $R_{SN}$. The resistor $R_{SN}$ may be coupled to a DC voltage source V1. In the exemplary embodiment of FIG. 2, $R_{SP}$ may have a value of 50Ω and $R_{SN}$ may have a value of 500Ω. The drain terminals of M1 and M2 may be coupled to the non-inverting terminal of operational amplifier A1, and the inverting terminal of A1 may be grounded. The output of the operational amplifier A1 may be coupled via resistor R1 to the gate terminal of MOSFET M1. In the exemplary embodiment of FIG. 2, resistor R1 has a value of 0.9 MΩ, though a different value may be used. The gate terminals of MOSFETs M1 and M2 may be coupled via capacitors C1 and C2. In the exemplary embodiment of FIG. 2, capacitor C1 has a value of 76 pF and capacitor C2 has a value of 30 pF, though other capacitances may be used.

The gate of MOSFET M2 may be coupled via a resistor R2 to the gate terminal of MOSFET M3. Resistor R2 may have a value of 0.9 MΩ, though a different value may be used. MOSFET M3 may be a p-type MOSFET, and its gate terminal may be coupled to its source terminal. The drain terminal of MOSFET M3 may be coupled to a resistor R3, which may have a value of 2 kΩ. Resistor R3 may be coupled to a DC voltage source V2 and to resistor $R_{SP}$.

The exemplary common-source amplifier circuit of FIG. 2 may also include a current source I1, which is coupled in parallel with capacitor C3, resistor R4, and oscillator X1. The current source I1 may be coupled to the source terminal of MOSFET M3 and to the node connecting capacitors C1 and C2.

The probe buffer may be implemented with a low-noise operational amplifier. However, the DC coupled differential input and multiple-stage amplifier of such an implementation consumes more than twice the power to achieve the same input referred voltage noise of the proposed transconductor structure shown in FIG. 2. Moreover, the DC coupled differential input stage is not necessary as the interfaces between piezoelectric or CMUT transducers to the probe buffer are likely AC coupled and single end. The total number of current branches of the proposed transconductor of FIG. 2 is reduced to one to minimize both input referred noise and power consumption.

In the transconductor probe buffer according to one or more exemplary embodiments, the transconductance gm may be constant and equal to gm1/(1+gm1*$R_{SN}$)+gm2/(1+gm2*$R_{SP}$). As shown in FIG. 3, the probe buffer output current is substantially flat from 1 MHz to 100 MHz. The maximum voltage signal at the probe buffer input is shown in FIG. 4 and can be as large as approximately ±500 mV, which corresponds to the output current range of ±11.7 mA. Even with the maximum voltage signal input, the second harmonic distortion is still lower than −60 dB.

The probe buffer output current $I_{OUT}$ according to an exemplary embodiment can be converted back to a voltage by a proper loading resistor (current-to-voltage conversion). It can be started with an input range $V_S$, with an output current range $I_{OUT}$=gm*$V_S$. The output current $I_{OUT}$ swing may result in a voltage span that is equal to the input range of the next stage amplifier $V_A$. In that case, the required value of the loading resistor, $R_L$, can be calculated as shown below in Equation (1):

$$R_L = \frac{V_A}{I_{OUT}} = \frac{V_A}{gm \cdot V_S} \quad (1)$$

Assuming that the next stage amplifier has the following values, $V_A$=±240 mV and VS=±500 mV, Equation (1) defines the value of the loading resistor as follows:

$$R_L = \frac{0.48}{gm} = 20.5\Omega \quad (2)$$

A voltage gain less than unity (0.48 in the above example) may not be desirable as it may cause the noise requirement of the next stage amplifier to be very stringent. But according to the exemplary embodiment, the probe buffer gain may be adjustable through the loading resistor. The resistance range may be limited by the maximum output current as well as the maximum output voltage. During operation, output current or voltage clippings might occur, which may generate excessive harmonics. Probe buffer gain switching through changing the loading resistor may also be feasible, although an extra external switch may be used here for varying the resistance.

For a high-impedance transducer, input current noise $I_N$ is dominating. As an example, the input referred current noise of a low noise amplifier may be characterized as 2.7 pA/√Hz. Then, given a transducer with 500Ω series resistance, the total equivalent input voltage noise is increased by $V_{Neq}$=R*$I_N$=1.35 nV/√Hz which is already larger than the 1 nV/√Hz full channel noise it claimed.

As mentioned, the electrical impedance matching at the receiver may be used to reduce reflections of the incoming acoustic energy back to the medium. In the case of the high-impedance transducer, the input impedance of the amplifier also may be high for the transducer termination. The exemplary embodiment of FIG. 2 shows a passive termination configuration with an external resistor and capacitor. Without termination, the input impedance of the probe buffer is approximately 10 kΩ (5 MΩ/15 pF) at 1 MHz.

For a low-impedance transducer, multiple probe buffers can be utilized in parallel to reduce the input referred voltage noise. These probe buffer outputs can be summed to achieve a desired transconductance. No AC coupling capacitors are required to block any DC component of the probe buffer outputs, which are essentially suppressed to 0V by low frequency feedback. Multiple probe buffer outputs can be summed together by simply connecting all of them together. Noise and power are traded off by the number of paralleled probe buffers while maintaining the bandwidth and linearity.

Figure 5:
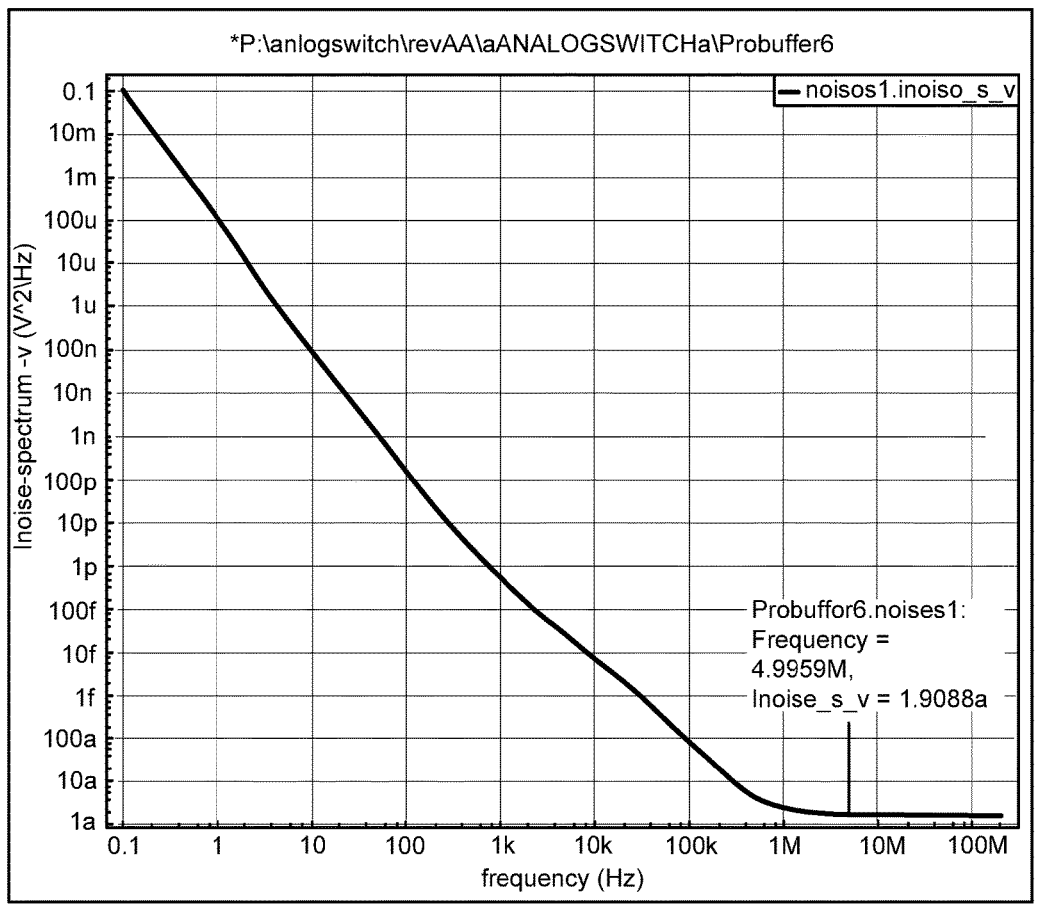
FIG. 5 depicts the input referred voltage noise power spectral density of the amplifier depicted in FIG. 2.

Each probe buffer may have a transconductance of 23.4 mA/V and power consumption of 10 mW. The total transconductance may be adjusted depending on signal strength and transducer sensitivity. For every additional probe buffer, the total transconductance may be increased by 23.4 mA/V. The gain of N paralleled probe buffers is determined by the product of the total transconductance N*gm and the loading resistance $R_L$. Thus, much higher gain can be obtained with the same loading resistor value. Higher than 6 dB gain is achieved by pairing two probe buffers while driving a 50Ω loading resistor. Input referred voltage noise, which is contributed to by both flicker and Johnson noises, appears between input and ground. The input referred voltage noise may have the RMS value of 1.38 nV/√Hz at T=300K for a single probe buffer, as shown in FIG. 5, and will also be reduced by a factor of √N. Due to process variation, the absolute transconductance tolerance could be high. The biasing circuit of FIG. 2 may be trimmed to set the transconductance in order to achieve better gm matching (across multiple probe buffer chips). Fortunately, the bandwidth and linearity are in the first order independent of total trans conductance.

Figure 6:
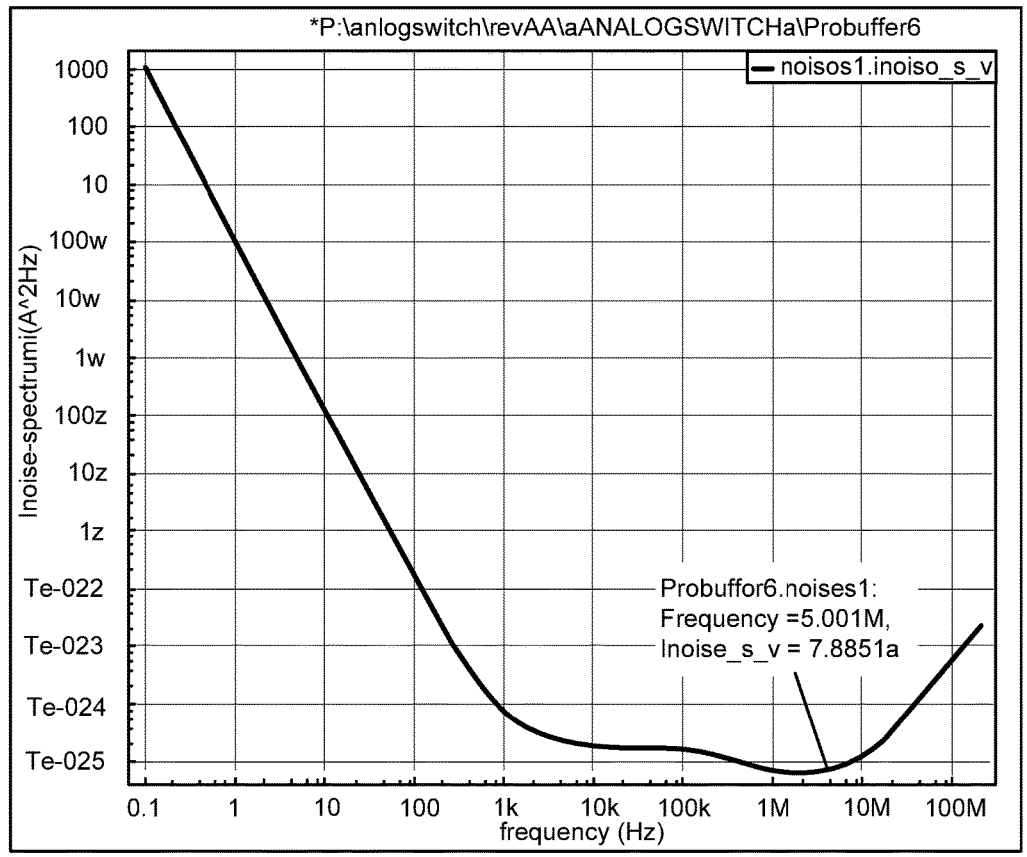
FIG. 6 depicts the input referred current noise spectral density of the amplifier depicted in FIG. 2.

Referring to FIG. 6, the input referred current noise power spectral density of the circuit of FIG. 2 is shown. The input referred current noise may have an RMS value of 0.28 pA/√Hz.

As the first stage of the ultrasound receiver, the amplifier may need to be able to withstand transmit pulses up to ±100V while efficiently passing the transmit current around the amplifier to the transducer element. While receiving, the amplifier will need to drive the capacitance of the cable while improving overall system noise and bandwidth.

Figure 7:
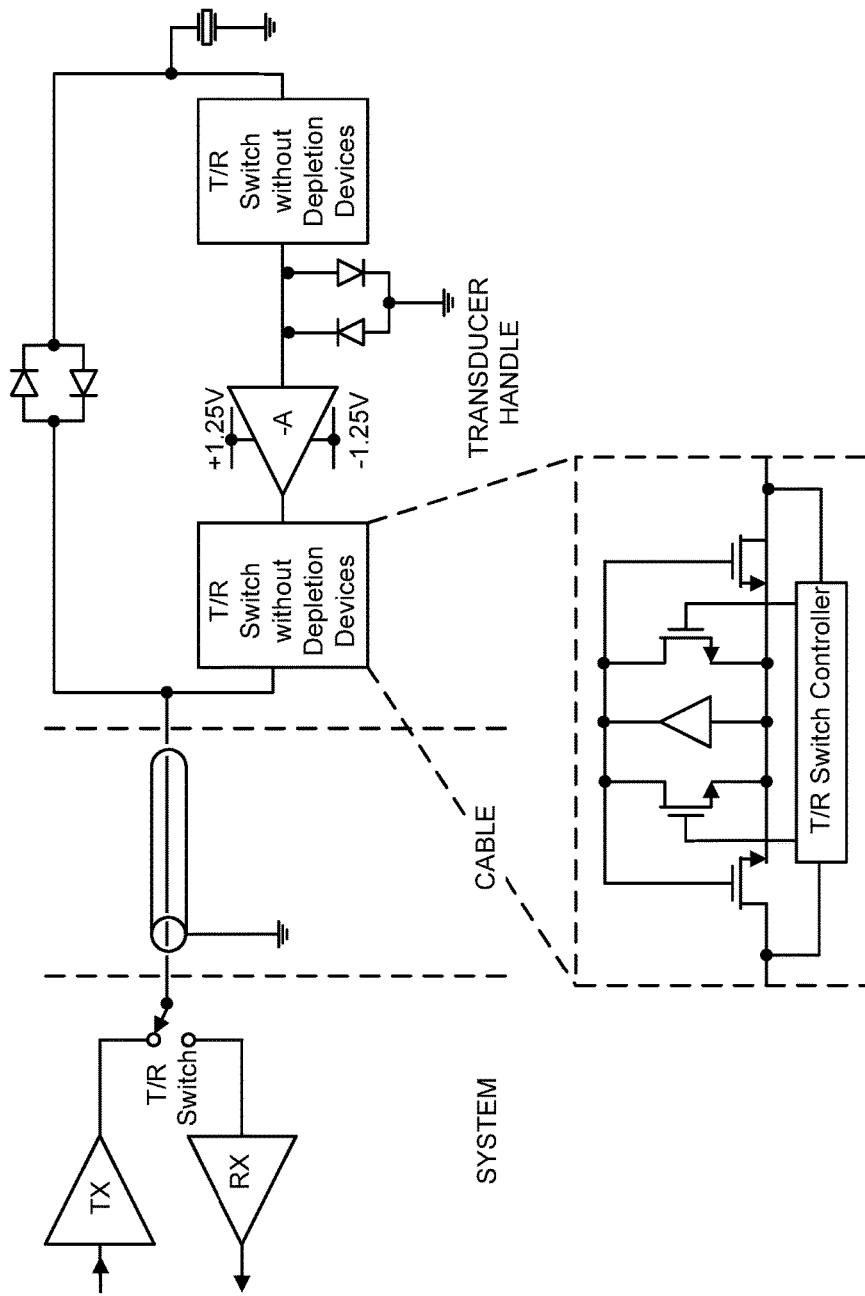
FIG. 7 depicts a block diagram of a single channel ultrasonic transducer according to an exemplary embodiment.

A single channel block diagram according to an exemplary embodiment is shown in FIG. 7. A transducer according to an exemplary embodiment may have 128 to 256 elements, although the number of elements is not necessarily limited thereto.

Since the probe buffer and the T/R switches may be mounted in the transducer handle, their footprints may be heavily constrained and integrating them in a single chip may be preferred. In order to meet these specifications, a high-voltage BCD process may be used. Even if the BCD process has the right voltage rating, the previous T/R switch design needs depletion-mode transistors which further complicate fabrication. Fortunately, the T/R switch could share the power supplies with the probe buffer or its accessory circuitry so as to get rid of the depletion-mode transistors, as long as the power budget of the whole channel is within 10 mW. In the design according to the exemplary embodiment, the probe buffer may consume the power of 8 mW, including the output DC biasing feedback circuitry and 1/16 share of constant gm current reference. To meet the stringent power requirements of the single ultrasound transducer channel, significant strides have been made in the T/R switch to achieve robust ultra low-power operation without depletion-mode devices. Prior to the exemplary embodiments of the present disclosure, each T/R switch circuit aimed at 1 mW power level. Using these circuit techniques disclosed herein, an integration of the probe buffer and the T/R switches with 10 mW power consumption per channel may be possible. The T/R switch on the input side of the probe buffer can have higher on-resistance since the probe buffer input is high impedance. This may help reduce the size of the channel.

Although the inventive concepts of the present disclosure have been described and illustrated with respect to exemplary embodiments thereof, it is not limited to the exemplary embodiments disclosed herein and modifications may be made therein without departing from the scope of the inventive concepts.

What is claimed is:

1. An ultrasound probe buffer comprising:
a high impedance amplifier having a common-source core stage with series-series local feedback;
wherein the high impedance amplifier comprises:
a first MOSFET and a second MOSFET, wherein a drain terminal of the first MOSFET is coupled to a drain terminal of the second MOSFET;
a first source degeneration resistor coupled to a source terminal of the first MOSFET;
a second source degeneration resistor coupled to a source terminal of the second MOSFET; and
an operational amplifier having a first input coupled to the drain terminal of the first MOSFET and the drain terminal of the second MOSFET;
wherein an output of the operational amplifier is coupled via a resistor to a gate terminal of the second MOSFET.

2. The ultrasound probe buffer of claim 1, wherein the resistance of the first source degeneration resistor is equal to the resistance of the second source degeneration resistor.

3. The ultrasound probe buffer of claim 1, wherein the high impedance amplifier outputs an output current from the drain terminals of the first MOSFET and the second MOSFET.

4. The ultrasound probe buffer of claim 1, wherein a gate terminal of the first MOSFET is coupled to a gate terminal of the second MOSFET via at least one capacitor.

5. The ultrasound probe buffer of claim 1, wherein the first MOSFET is a p-type MOSFET and the second MOSFET is an n-type MOSFET.

6. The ultrasound probe buffer of claim 1, wherein the transconductance of the ultrasound probe buffer is substantially constant.

* * * * *